United States Patent [19]

Hössel et al.

[11] Patent Number: 6,007,801
[45] Date of Patent: *Dec. 28, 1999

[54] USE OF CARBOXYL-CONTAINING POLYSILOXANES IN COSMETIC FORMULATIONS

[75] Inventors: Peter Hössel, Schifferstadt; Michael Kneip, Ludwigshafen; Norbert Greif, Bobenheim, all of Germany

[73] Assignee: BASF Aktiengesellschaft, Ludwigshafen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/935,658

[22] Filed: Sep. 23, 1997

[51] Int. Cl.$^6$ ........................................................ A61K 7/06
[52] U.S. Cl. ................................. 424/70.122; 424/70.12; 528/28
[58] Field of Search ............................ 424/70.122, 70.12; 528/28

[56] References Cited

U.S. PATENT DOCUMENTS

| 4,523,921 | 6/1985 | Sebag et al. | 8/405 |
| 4,533,714 | 8/1985 | Sebag et al. | 528/27 |
| 4,587,321 | 5/1986 | Sebag et al. | 528/27 |
| 4,609,750 | 9/1986 | Killmeier et al. | 556/419 |
| 4,844,888 | 7/1989 | Zawadzki | 429/69 |
| 4,931,062 | 6/1990 | Bay et al. | 8/94.23 |
| 5,160,730 | 11/1992 | Dubief et al. | 424/59 |
| 5,756,080 | 5/1998 | Janchitraponvej et al. | 424/70.122 |

FOREIGN PATENT DOCUMENTS

| 324 345 | 7/1989 | European Pat. Off. . |
| 2443476 | 7/1980 | France . |
| 0 017 121 | 10/1980 | Germany . |
| 33 40 708 | 5/1984 | Germany . |

OTHER PUBLICATIONS

Kollmeier et al., *Soap, Perfumery & Cosmetics*, vol. 72, No. 7, Jul. 1, 1985, pp. 371–377.

Primary Examiner—David W. Wu
Attorney, Agent, or Firm—Keil & Weinkauf

[57] ABSTRACT

A cosmetic composition comprising a carboxyl-containing polysiloxane and a cosmetically acceptable auxiliary; in which the carboxyls are amidated by a compound selected from the group consisting of 2-amino-2-methyl-1-propanol, ethanolamine, morpholine and triethanolamine, and said amidation is up to 50 mol % of the carboxyls.

4 Claims, No Drawings

USE OF CARBOXYL-CONTAINING POLYSILOXANES IN COSMETIC FORMULATIONS

This is a continuation application under 37 CFR 1.53(d) (continued prosecution application (CPA)) of prior application Ser. No. 08/935,658, filed on Sep. 23, 1997.

The present invention relates to the use of carboxyl-containing polysiloxanes in cosmetic formulations, especially in skincare and haircare products.

DE-A-3340708 describes quaternized polysiloxane polymers and cosmetic compositions comprising them, such as shampoos and rinsing lotions. The haircare properties of these polymers, however, are not adequate, especially in respect of the care of heavily damaged hair after hair bleaching.

EP-A-324345 describes a process for the hydrophobization of leather and pelts with a carboxyl-containing polysiloxane in which the carboxyls are in neutralized form.

It is an object of the present invention to develop a polysiloxane-based polymer for cosmetic formulations which in terms of its skincare and haircare effect is superior to the materials of the prior art.

We have found that this object is achieved by the use in cosmetic formulations of carboxyl-containing polysiloxanes of which from 0 to 50 mol-% of the carboxyls have been amidated.

The carboxyl-containing polysiloxanes used in accordance with the invention are known to the skilled worker. Particularly suitable polysiloxanes are those in which the remaining valencies of the silicon are satisfied by aliphatic or aromatic hydrocarbon radicals, especially methyl but also ethyl, propyl or phenyl, and which deriving from their preparation contain carboxylic acid or carboxylic anhydride groups incorporated into the molecule, at the ends and/or in the side chains, via these hydrocarbon radicals. The carboxyl-containing polysiloxanes used in accordance with the invention preferably contain on average from 2 to 10 carboxyls per molecule.

Particularly preferred carboxyl-containing polysiloxanes are dimethylpolysiloxanes and methylpropylpolysiloxanes containing terminal carboxylic anhydride groups. Very particular preference is given to dimethylpolysiloxanes and methylpropylpolysiloxanes containing terminal succinic anhydride groups.

For the amidation and subsequent neutralization of the existing carboxyls and for the hydrolysis and neutralization of anhydride groups present, the polysiloxanes are judiciously reacted in aqueous or alcoholic solution with a base or with an amine until a pH of 7–10, preferably 7–8.5, is established. It is also possible to use a mixture of amine and a base such as alkali metal hydroxide.

Alternatively, the carboxyls can be amidated and neutralized separately. In this case some of the carboxyls are first of all converted with an amine or a mixture of various amines to the corresponding amide or the corresponding amides, respectively, and then some or all of the remaining free carboxyls are neutralized with a base, an amine, a mixture of different amines or a mixture of the components mentioned.

Alternatively, the reaction with the amine can be carried out directly without solvent.

With particular preference the polysiloxanes which carry carboxylic anhydride groups are reacted in the presence of amines, amino alcohols or mixtures thereof, so that the anhydrides are amidated with ring opening.

In the amidation reaction, from 0 to 50 mol-% of the carboxyls are converted to the amide. The degree of conversion to the amide is preferably from 5 to 50 mol-%, particularly preferably from 20 to 50 mol-% and, with particular preference, from 40 to 50 mol-%.

In the subsequent neutralization of the remaining free carboxyls with base or amine, from 0 to 100 mol-% of the free carboxyls are neutralized. In this context the proportion of the amine in the neutralizing agent should judiciously be such that at least 50 mol-%, preferably at least 70 mol-% and, with particular preference, 80–100 mol-% of the free carboxyls are neutralized with amine. Neutralization of the carboxyl-containing polysiloxanes can also be carried out without prior amidation.

Amines which can be employed are all primary, secondary or tertiary amines or mixtures thereof. Preference is given to primary or tertiary amines, since the secondary amines can undesirably form nitrosamines. However, in principle the reaction can also be carried out with secondary amines. Suitability extends, furthermore, to amino-containing alcohols, such as mono-, di- or trialkanolamine with 2–6 carbons in the alkanol residue, examples being mono-, di- and triethanolamine.

Particularly suitable amines are morpholine, ethanolamine, 2-amino-2-methyl-1-propanol and mixtures thereof, especially ethanolamine, 2-amino-2-methyl-1-propanol and mixtures thereof with other amines and bases.

Amidation and/or neutralization of the carboxyls with the amines are preferably conducted at from 20 to 130° C., preferably at 40 to 100° C.

The invention provides for the use of such carboxyl-containing polysiloxanes for cosmetic formulations, especially for skincare and haircare compositions.

The carboxyl-containing polysiloxanes are preferably used as hairsetting products, as conditioners, as thickeners and as auxiliaries in coloring, bleaching and permanently waving the hair.

With particular advantage the carboxyl-containing polysiloxanes are employed in the form of emulsions. These emulsions can comprise all auxiliaries and active ingredients which are customary in cosmetology.

Usually, emulsifying substances are brought together with water, oils, fats and, possibly, fatty alcohols, fatty acids, preservatives, polymers, consistency regulators and gel formers.

Active substances that may be present include photoprotectants, bleaches, hair colorants, permanent waving substances, cationic surfactants, anionic surfactants, humectants, urea, vitamins, panthenol, panthenol ethyl ether and/or bisabolol.

The invention also provides for the use of the carboxyl-containing polysiloxanes in oral care compositions and in nailcare of the fingers and toes.

For the novel use it is possible to employ, alongside the carboxyl-containing polysiloxanes, all constituents which are normally used in cosmetic compositions, especially ionic and nonionic surfactants, foam synergists, foam stabilizers, opacifiers, sequesterants, thickeners, emulsifiers, softeners, preservatives, protein derivatives, natural substances, colorants, perfumes and, if appropriate, further polymers or auxiliaries.

EXAMPLES 1–4

Preparing Polymer 1

30 g of morpholine and 3 g of oleic acid are added at 60° C. to 167 g of silicone oil IM 86 (Wacker) and the mixture is stirred at 60° C. for 60 minutes. The IR spectrum of the reaction product no longer has an anhydride band at 1780 cm⁻¹. About 800 ml of water are added, the mixture is preemulsified with an Ultraturrax, and then full emulsification is carried out at 150 bar using a high-pressure emulsifier.

Preparing Polymer 2

Ethanolamine as Amine Component 24.4 g of ethanolamine are added dropwise at <70° C. and with stirring to 211.2 g of silicone oil IM 86. The mixture is subsequently stirred at the temperature indicated above for two hours. 2.65 g of oleic acid are added to the resulting reaction mixture, and this mixture is used to prepare an emulsion. For this purpose, 800 ml of water are added to 200 g of the product, and the mixture is preemulsified using an Ultraturrax and then emulsified at 150 bar by means of a high-pressure emulsifier.

Preparing Polymer 3

2-amino-2-methyl-1-propanol as Amine Component

The preparation is as described for polymer 2, reacting 209.2 g of silicone oil IM 86, 36.3 g of 2-amino-2-methyl-1-propanol and 2.65 g of oleic acid.

Preparing Polymer 4

Morpholine and 2-amino-2-methyl-1-propanol as Amine Components 10.8 g of morpholine are added dropwise over the course of 15 minutes at <70° C. and with stirring to 182.1 g of silicone oil IM 86, and the mixture is subsequently stirred at 60° C. for 30 minutes. The IR spectrum of the reaction mixture no longer has an anhydride band at 1780 cm⁻¹. 16 g of 2-amino-2-methyl-1-propanol are added to the resulting reaction product, and the mixture is stirred at 60° C. for 1.5 hours. Following the addition of 2.4 g of oleic acid and 845 g of water, the product is used as described above to prepare an emulsion.

Process Variant for Preparing the Novel Compounds

The novel compounds can also be prepared by methods other than those indicated in the examples. For instance, one advantageous process variant consists in taking the amine component together with oleic acid in aqueous solution as initial charge and adding the anhydride-functionalized polysiloxane dropwise at <70° C. Subsequent processing to the emulsion, after the reaction is over, is then carried out similarly to the procedure already described.

EXAMPLE 5

Preparing Two Emulsions

The two emulsions 1 and 2 were prepared and their haircare properties were examined.

| Emulsion 1 | g | INCI Name |
|---|---|---|
| Phase A: | 1.00 | Silicone derivative (active ingredient) |
| | 1.50 | Ceteareth-25 |
| | 1.50 | Ceteareth-6 and stearyl alcohol |
| | 6.00 | Cetearyl octanoate |
| | 3.00 | Cetearyl alcohol |
| Phase B: | 2.00 | Propylene glycol |
| | 0.30 | Imidazolidinyl urea |
| | 0.10 | Benzyl alcohol, methylchloroisothiazolinone, methylisothiazolinone |
| | ad 100.00 g | Water |

| Emulsion 2 | g | INCI Name |
|---|---|---|
| Phase A: | 1.50 | Ceteareth-25 |
| | 1.50 | Ceteareth-6 and stearyl alcohol |
| | 6.00 | Cetearyl octanoate |
| | 3.00 | Cetearyl alcohol |
| Phase B: | 1.00 | Silicone derivative (active ingredient) |
| | 2.00 | Propylene glycol |
| | 0.30 | Inidazolidinyl urea |
| | 0.10 | Benzyl alcohol, methylchloroisothiazolinone, methylisothiazolinone |
| | ad 100.00 g | Water |

Phase A and B were heated separately to 80° C. with stirring. Phase A was added to Phase B, with stirring, and the mixture was cooled.

Following preparation, the pH was adjusted with citric acid.

Tests:

Wet combability: subjective assessment on locks of hair by trained and experienced hairdressing and laboratory personnel. Rating scale: 1 (very good), 2 (good) and 3 (poor) Duplicate determination by two individuals on bleached locks of mid-European hair; width 6 cm, length 25 cm.

Decrease in combing force: Testing of the wet combability on a tensile/pressure testing machine. Measurement of the decrease in combing force in comparison with an untreated lock of hair. Mean value from 15 individual measurements: hair as above.

Static charging: subjective assessment by trained, experienced hairdressing and laboratory personnel after combing the abovementioned locks of hair 10 times in the dry state in a climatically controlled room at 50% relative humidity.

Rating scale: 1 (none); 2 (slight); 3 (severe)

Feel of the dry hair: subjective assessment by trained, experienced hairdressing and laboratory personnel.

Rating scale: 1 (very soft), 2 (soft), 3 (rough)

TABLE 1

Results of the performance tests

| Polymer No. | Emulsion No. | pH | Wet combability (rating) | % Decrease in combing force | Static charging | feel (rating) |
|---|---|---|---|---|---|---|
| Polymer No. | | | | | | |
| 1 | 2 | 2–3 | 1–2 | 54 | 1 | 2 |
| 2 | 2 | 2–3 | 1–2 | 69 | 1 | 2 |
| 3 | 2 | 6–7 | 1 | 63 | 1 | 1 |
| 3 | 2 | 2–3 | 1 | 64 | 1 | 1 |
| 4 | 2 | 6–7 | 1–2 | — | 1 | 2 |
| 4 | 2 | 2–3 | 1–2 | — | 1 | 2 |
| Comparison Examples: | | | | | | |
| no polymer | no polymer | 2–3 | 2–3 | 0 | 3 | 3 |
| Quaternium-80 | 1 | 2–3 | 2–3 | 25 | 3 | 3 |
| Dimethicone copolyol | 1 | 2–3 | 2–3 | 16 | 3 | 3 |
| Poly-quaternium-11 | 2 | 2–3 | 2 | 36 | 3 | 2 |
| Dimethicone propyl PG-betaine | 1 | 2–3 | 3 | 11 | 3 | 3 |
| Dimethicone propyl PG-betaine | 2 | 2–3 | 3 | 17 | 3 | 3 |

We claim:

1. A cosmetic composition comprising a carboxyl-containing polysiloxane and a cosmetically acceptable auxiliary; in which the carboxyls of the polysiloxane are amidated by a compound selected from the group consisting of 2-amino-2-methyl-1-propanol, ethanolamine, morpholine and triethanolamine, and said amidation is up to 50 mol % of the carboxyls.

2. The composition of claim 1 wherein the carboxyl-containing polysiloxane is a dimethylsiloxane.

3. A process for preparing an amidated, carboxyl-containing polysiloxane, which process comprises amidating up to 50 mol-% of the carboxyls of the carboxyl-containing polysiloxane with a compound selected from the group consisting of 2-amino-2-methyl-1-propanol, ethanolamine, morpholine and triethanolamine; and recovering the amidated carboxyl-containing polysiloxane.

4. The process of claim 3 in which the carboxyl-containing polysiloxane is a dimethylsiloxane.

* * * * *